(12) United States Patent
Whiting et al.

(10) Patent No.: US 9,895,506 B2
(45) Date of Patent: Feb. 20, 2018

(54) PRESSURE ADJUSTMENT METHOD FOR CPAP MACHINE

(71) Applicant: Fisher & Paykel Healthcare Limited, Auckland (NZ)

(72) Inventors: David Robin Whiting, Auckland (NZ); Andrew Gordon Gerred, Auckland (NZ); Fiona Elizabeth Cresswell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 15/153,278

(22) Filed: May 12, 2016

(65) Prior Publication Data

US 2017/0100555 A1 Apr. 13, 2017

Related U.S. Application Data

(63) Continuation of application No. 14/673,242, filed on Mar. 30, 2015, now Pat. No. 9,339,619, which is a continuation of application No. 12/975,015, filed on Dec. 21, 2010, now Pat. No. 8,991,392.

(51) Int. Cl.
*A61M 16/00* (2006.01)
*A61B 5/00* (2006.01)
*A61M 16/16* (2006.01)

(52) U.S. Cl.
CPC ....... *A61M 16/0069* (2014.02); *A61B 5/4818* (2013.01); *A61B 5/4836* (2013.01); *A61M 16/16* (2013.01); *A61M 2016/003* (2013.01); *A61M 2016/0027* (2013.01)

(58) Field of Classification Search
CPC .............. A61M 16/00; A61M 16/0051; A61M 16/0057–16/0072; A61M 16/10; A61M 2016/0015–2016/0042; A61M 2230/40–2230/42; A62B 7/00–7/04
See application file for complete search history.

(56) References Cited

U.S. PATENT DOCUMENTS

| | | |
|---|---|---|
| 5,551,419 A | 9/1996 | Froehlich et al. |
| 6,739,335 B1 | 5/2004 | Rapport et al. |
| 8,220,457 B2 | 7/2012 | Berthon-Jones et al. |
| 8,991,392 B1 | 3/2015 | Whiting et al. |
| 9,339,619 B2 | 5/2016 | Whiting et al. |
| 2006/0000475 A1 | 1/2006 | Matthews |
| 2007/0129647 A1 | 6/2007 | Lynn |
| 2009/0038616 A1 | 2/2009 | Mulcahy et al. |
| 2009/0139523 A1 | 6/2009 | Ayappa et al. |
| 2011/0192400 A9 | 8/2011 | Burton et al. |
| 2012/0291783 A1 | 11/2012 | Peiris et al. |

*Primary Examiner* — Rachel Young
(74) *Attorney, Agent, or Firm* — Knobbe, Martens, Olson & Bear, LLP

(57) ABSTRACT

A positive airway pressure apparatus is automatically adjusting. Pressure increases in response to apnea events when the apparatus is in one or more responsive states. Pressure does not increase in response to apnea events when the apparatus is in a non-responsive state. The apparatus switches between responsive and nonresponsive states depending upon any of a number of different criteria that help differentiate between open airway apnea events and closed airway apnea events.

13 Claims, 8 Drawing Sheets

PRESSURE ADJUSTMENT METHOD FOR CPAP MACHINE

CROSS-REFERENCE TO RELATED APPLICATIONS

This application is a continuation of U.S. patent application Ser. No. 14/673,242, filed Mar. 30, 2015, which is a continuation of U.S. patent application Ser. No. 12/975,015, filed Dec. 21, 2010 (now issued as U.S. Pat. No. 8,991,392), each of which are hereby incorporated by reference in their entirety.

BACKGROUND OF THE INVENTION

Field of the Invention

The present invention relates to systems for treating obstructive sleep apnea by providing positive airway pressure to a patient, in particular, to methods for the device to adjust the treatment pressure in response to breathing events.

Description of the Related Art

One major treatment approach for obstructive sleep apnea includes providing breathing gases to the patient throughout the period the patient is asleep. These treatments may collectively be known as positive airway pressure therapy (PAP). Variations on this therapy include having different inspiration and expiration pressures, commonly known as bi-level or bi-PAP, or having continuously adjusting therapy which responds to breathing events.

Self-adjusting or self-titrating PAP systems typically increase the treatment pressure in response to events, and decrease the treatment pressure in response to periods of normal breathing. Events for which the systems increase pressure can include apneas, hypopneas and obstructed breathing. Many different methods have been provided for determining the occurrence of an apnea, a hypopnea or obstructed breathing. For example, our U.S. patent application Ser. No. 11/198,072 describes a system that determines events by analysing a flow signal provided by a flow sensor. The system determines an apnea based on a period where the flow signal indicates a lack of patient breathing. The system determines a hypopnea based on a period of reduced breathing volume. The system determines obstructed breathing on analysis of the discreet energy spectrum of the flow signal of patient breaths. The system modifies the treatment pressure depending on the present pressure and the determined event. When responding to apneas or hypopneas, the described system only increases the pressure if the present treatment pressure is below 10 cmH2O. When responding to flow limitations and obstruction, the system will always increase pressure, subject to an overall maximum allowed pressure.

An upper limit for responding to apneas and hypopneas that are not accompanied by a flow limitation is to recognise that not all events are caused by obstruction and collapsing airways which can be alleviated with increased pressure. Instead, some events, commonly referred to as "central" events, do not respond to increases in pressure. Many CPAP patients suffer from both obstructive events and central events. Although increasing the treatment pressure in response to central events is not usually dangerous, it is believed that it could trigger additional central events or rouse the patient. This is generally thought more likely with higher CPAP pressures, and the likelihood that an event is central is generally thought more likely at higher treatment pressures.

Nonetheless, a defined threshold may not be the optimal solution for deciding whether to increase the pressure in relation to apneas and non flow-limited hypopneas. In some cases, where central apneas are being experienced at lower pressures, this system will allow the CPAP pressure to reach a level that is not required. In other cases, the threshold pressure may be reached with the patient still incurring obstructed apneas that could respond to further increases in pressure.

Methods have been devised to attempt to differentiate between open airway apneas, which are unlikely to respond to increases in PAP pressure and closed airway apneas, which may respond to an increase in therapy pressure. These include analysing the flow in pressure signals to determine the presence of airflow, that is airflow that is generated by the beating heart which can slightly affect the lung volume. Another method involves examining the airway response to a forced oscillation or probing signal. Both these methods add complexity to the system and may not be fully reliable across a wide range of patients.

SUMMARY OF THE INVENTION

An object of the present invention is to provide a control method, or a PAP system including a control method, which goes some way toward overcoming the above disadvantages or which will at least provide the public with a useful choice.

In one aspect, the present invention may broadly be said to consist in an apparatus comprising a gases flow source including a blower supplying an outlet which in use is connected to a patient, a sensor for sensing pressure or flow or both, supplied by the blower, a controller receiving output from the sensor, and controlling the output of the blower, the controller determining at least apnea, non-flow limited hypopnea, or flow limited breaths from the output of the sensor, the controller performing a control method including a sequence of states in which the controller will or will not respond to non-isolated apneas by increasing the output of the blower, the sequence including at least two responsive states in which the controller may respond to an apnea, or to a non-flow limited hypopnea or to a flow limited breath by increasing pressure, but in the case of an apnea only when the apnea was preceded within a defined period by another apnea or a non-flow limited hypopnea, at least two non-responsive states in which it will not respond to an apnea increasing pressure; the control method switches from responsive states to non-responsive states according to function of both elapses of time in the responsive state without events, and accumulated apneas and non-flow limited hypopneas since entering the responsive state; the control method switches from a first non-responsive state to a responsive state by one or more of the following elapse of time in the non-responsive state, sensing patient arousal, elapse of time without apneaic events; and the control method switches from a second non-responsive state to a responsive state by one or more of the following elapse of time in the non-responsive state, sensing patient arousal and not based only on a elapse of time without apneaic events; such that a long sequence of consecutive non-isolated apneas leads the control to adopt, in order, a responsive state, the first non-responsive state, another responsive state and the second non-responsive state; and results in a first sequence of output increases, a pause, a second sequence of output increases and then an indefinite suppression of further increases.

In a further aspect, the present invention may broadly be said to consist in an apparatus comprising a gases flow source supplying an outlet which in use is connected to a patient, a sensor for sensing pressure or flow or both, supplied by the flow source or supplied to the patient, a controller receiving output from the sensor, and controlling the output of the flow source, the controller determining at least apnea events from the output of the sensor, the controller performing a control method including one or more responsive states in which it may respond to an apneaic event by increasing pressure, non-responsive states in which it will not respond to an apneaic event by increasing pressure; the control method switches from a non-responsive state to a responsive state by one or more of the following, depending on the responsive state elapse of time in the non-responsive state, sensing patient arousal, elapse of time without apneaic events; and the control method switches from a responsive state to a non-responsive state by a function of both: elapse of time in the responsive state without events, and accumulated apneaic events since entering the responsive state.

According to a further aspect, the gases flow source comprises a blower and the output of the blower is controlled by the controller.

According to a further aspect, the gases flow source includes a humidifier and power input to the humidifier is controlled by the controller.

According to a further aspect, the sensor is a flow sensor.

According to a further aspect, the controller maintains desired pressure data representing a desired treatment pressure and the controller controls the output of the source according to the desired pressure data.

According to a further aspect, the apparatus includes a pressure sensor for sensing pressure supplied by the flow source and the controller controls the output of the flow source with a feedback control to maintain the output according to the desired pressure data.

According to a further aspect, apneaic events include apnea and non-flow limited hypopnea.

According to a further aspect, the controller also determines flow limited breaths, and responds to determinations of flow limited breaths with increases in pressure.

According to a further aspect, the apparatus includes two different response states, one of which may be followed by a first non-responsive state that can be exited by lapse of time (with or without apneaic events), and the other is entered from the first non-responsive state.

According to a further aspect, the other response state may be followed by a non-responsive state that can only be exited by elapse of time without apneaic events, or by sensing patient arousal.

According to a further aspect, the controller responds to an apneaic event only if it is preceded by another apneaic event in a defined period.

According to a further aspect, the defined period is between 2 minutes and 3 minutes.

According to a further aspect, the controller will respond to flow limited breaths in both the responsive and non-responsive states.

According to a further aspect, for one non-responsive state, the controller will exit the non-responsive state after an elapse of between 3 and 7 minutes (with or without apneaic events).

According to a further aspect, the controller exiting a non-responsive state in response to patient arousal also reduces the delivered therapy pressure.

According to a further aspect, the controller will exit a non-responsive state due to an elapse of time without apneaic events once the desired pressure level returns to a minimum pressure.

According to a further aspect, the controller switches from a responsive state to a non-responsive state if an accumulation of non-isolated apneaic events exceeds an accumulation of normal breathing by a predetermined amount.

According to a further aspect, in the absence of nominal periods of normal breathing, the predetermined amount triggers a non-responsive period after three non-isolated events.

According to a further aspect, the controller reduces the pressure by 0.5 $cmH_2O$ each 2.5 minute period without events.

According to a further aspect, the controller raises the pressure by an increase of 1 $cmH_2O$ when responding to an apneaic event.

In a further aspect, the present invention may broadly be said to consist in a control method for a controller in an automatically adjusting PAP apparatus, including one or more responsive states in which it may respond to an apneaic event by increasing pressure; non-responsive states in which it will not respond to an apneaic event by increasing pressure; the control method switches from a non-responsive state to a responsive state by one or more of the following, depending on the responsive state elapse of time in the non-responsive state, sensing patient arousal, elapse of time without apneaic events; and the control method switches from a responsive state to a non-responsive state by a function of both elapse of time in the responsive state without events, and accumulated apneaic events since entering the responsive state.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

One preferred embodiment of the present invention will be described with reference to the accompanying drawings.

DETAILED DESCRIPTION OF THE PREFERRED EMBODIMENT

The present invention relates to particular aspects of a self-adjusting therapy device. In particular, the present invention provides control principles that adapt how the device adjusts the treatment pressure in response to apneas and non flow-limited hypopneas. One principle of this control is that the response to apneas and non flow-limited hypopneas operate independently to the response for other events, including flow limited breaths and flow-limited hypopneas and periods of normal breathing.

According to this control strategy for apneas and non flow-limited hypopneas, certain patterns of events are determined and responded to by entering a non-responsive state. In the non-responsive state, the control will not increase the treatment pressure in response to another apnea, but will increase the treatment pressure in response to any other event including flow-limited breaths, flow-limited hypopneas or non flow-limited hypopneas. Preferably, the control provides an independent pressure limit for the response to non flow-limited hypopneas.

According to another principle, the control does not respond to isolated apneas. The control will only respond to an apnea if the apnea occurs within a predetermined time of another apnea or within a predetermined time of a non flow-limited hypopnea.

According to another principle, the device provides a limited response to a string of rapidly occurring apneas or non flow-limited hypopneas. In particular, the control enters a pause state if the total number of non isolated apneas and hypopneas less any number of nominal periods of normal breathing exceeds a threshold value, for example, "3". This threshold is not directly related to any pressure increase. Pressure increases over this period may have been larger due to additional flow-limited events or smaller, due to the limit on response to non flow-limited hyponeas.

According to a further principle, the control will respond to two such chains of apnea, with an intervening pause state, and then enter a longer term non-responsive state. The longer term non-responsive state will inhibit response to apneas until the set pressure reduces below a threshold, due to periods of normal breathing.

To understand the effect of this control, the control must be considered as an overlay on the concurrent responses being provided to normal breathing, obstructed breathing, flow-limited hypopneas and non flow-limited hypopneas.

In the preferred control, the only limitation to response to flow-limited breaths is an overall maximum therapy pressure. This applies also to flow-limited hypopneas. The only limitation on response to non flow-limited hypopneas is a pressure limit operating independently of the apnea control.

Figure 2:
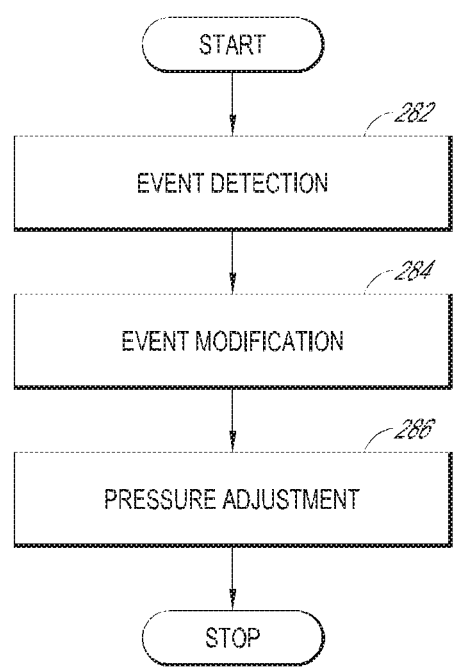
FIG. 2 is a schematic diagram illustrating an overall pressure adjusting algorithm.

According to this, the apnea response algorithm can operate quite independently of how the device responds to other OSA events. An example apnea response algorithm will be described on that basis. This algorithm is illustrated in FIG. 4 and is indicated by box 284 in FIG. 2. As indicated in FIG. 2, the apnea response process 284 operates as a periodic control loop that sits between an event detection procedure 282 and a pressure adjustment procedure 286. The event detection loop 282 provides an event variable (Event), or a set of event flags which indicate the determination of certain OSA events, including apnea, non flow-limited hypopnea, normal breathing, no event, and other events (which might include flow-limited hypopneas, flow-limited breaths, arousals or snoring).

In the pressure adjusting algorithm 286, the set pressure is incremented or decremented according to the event variable. Typically, this involves an increase in pressure for OSA events such as apneas, hypopneas, flow-limited breaths, flow-limited hypopneas and snoring, a decrease in pressure in response to sustained periods of normal breathing or patient arousals, and maintaining the present set pressure when the Event returns "none".

The presently described apnea control sits between the event determination algorithm and the pressure adjustment algorithm and modifies the value of Event by replacing "apnea" events with "none" under some circumstances.

In considering the described control, it is important to note that the example algorithm is repeated frequently and rapidly. For example, the full algorithm might be repeated every 20 ms to 50 ms. This is more than ten times the frequency of patient breathing and means that events other than "none" are comparatively rare, and the normal status for the Event is "none". For example, in a typical event determination algorithm, "normal breathing" might be returned after a predetermined period without any OSA events or arousals, and this predetermined period might be between 2 and 5 minutes. If this predetermined period is 2.5 minutes and the repeat frequency of the apnea response algorithm is 20 ms, then a return of "normal breathing" will be preceded by 7,500 executions where the Event is "none". Similarly, an apnea might be determined in response to 10 seconds without a detected breath. During this period, the event determination algorithm may be returning "none", meaning 500 "none" returns.

According to this example, the apnea detection algorithm only returns "apnea" once for any single period of non-breathing. For example, the apnea detection may return "apnea" after a predetermined trigger period without detected breathing. The apnea detection algorithm then returns "none" until breathing resumes or another independent event occurs.

Even a single flow-limited breath would require 1 to 1.5 seconds, and therefore be preceded by 50 to 75 "none" returns.

The described apnea response algorithm is structured accordingly. However, other control approaches could be developed using the principles outlined earlier. For example, the principles could be integrated into an interrupt-based response system, where a piece of pressure adjustment code is executed only when an event other than "none" is returned. The adjustment code would then review a history of events to determine the outcome for the event concerned.

In most executions of the described apnea response algorithm, there is either no effect, or the only effect is to decrement a timer by an amount reflecting the time since the previous execution.

Figure 3A:
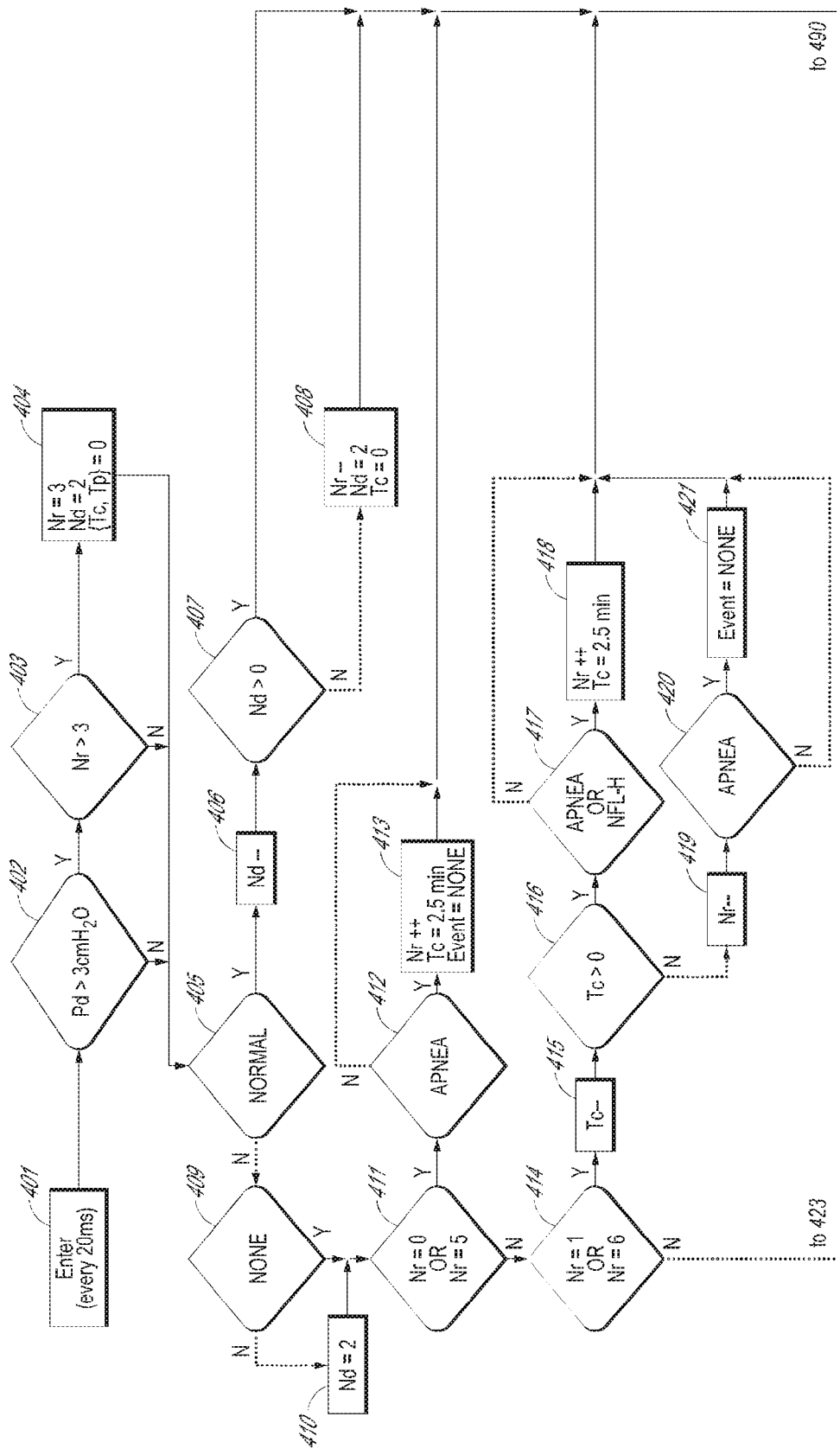
FIGS. 3a to 3c is a schematic diagram illustrating an algorithm that adjusts the response to apneas.
Figure 3B:
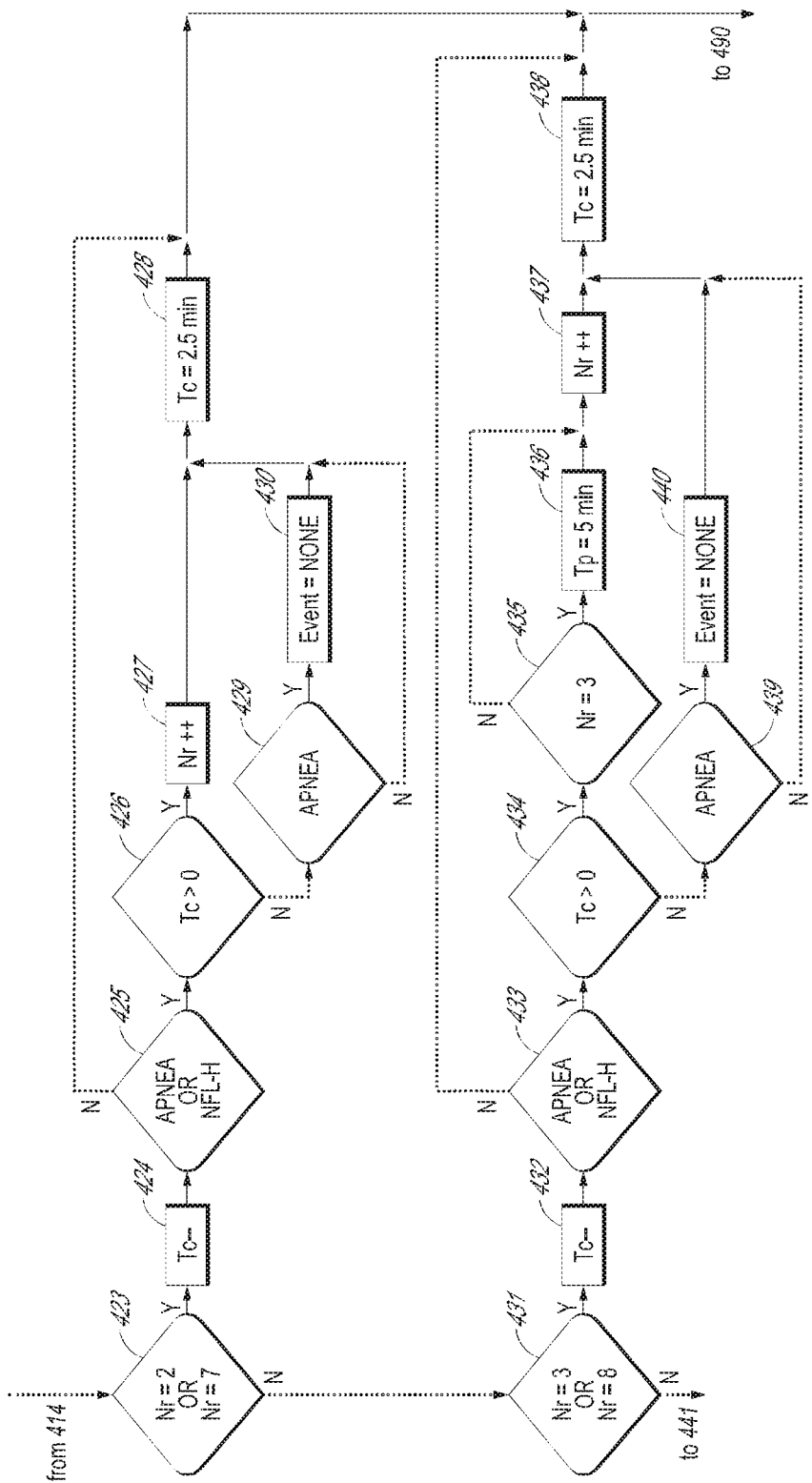
Figure 3C:
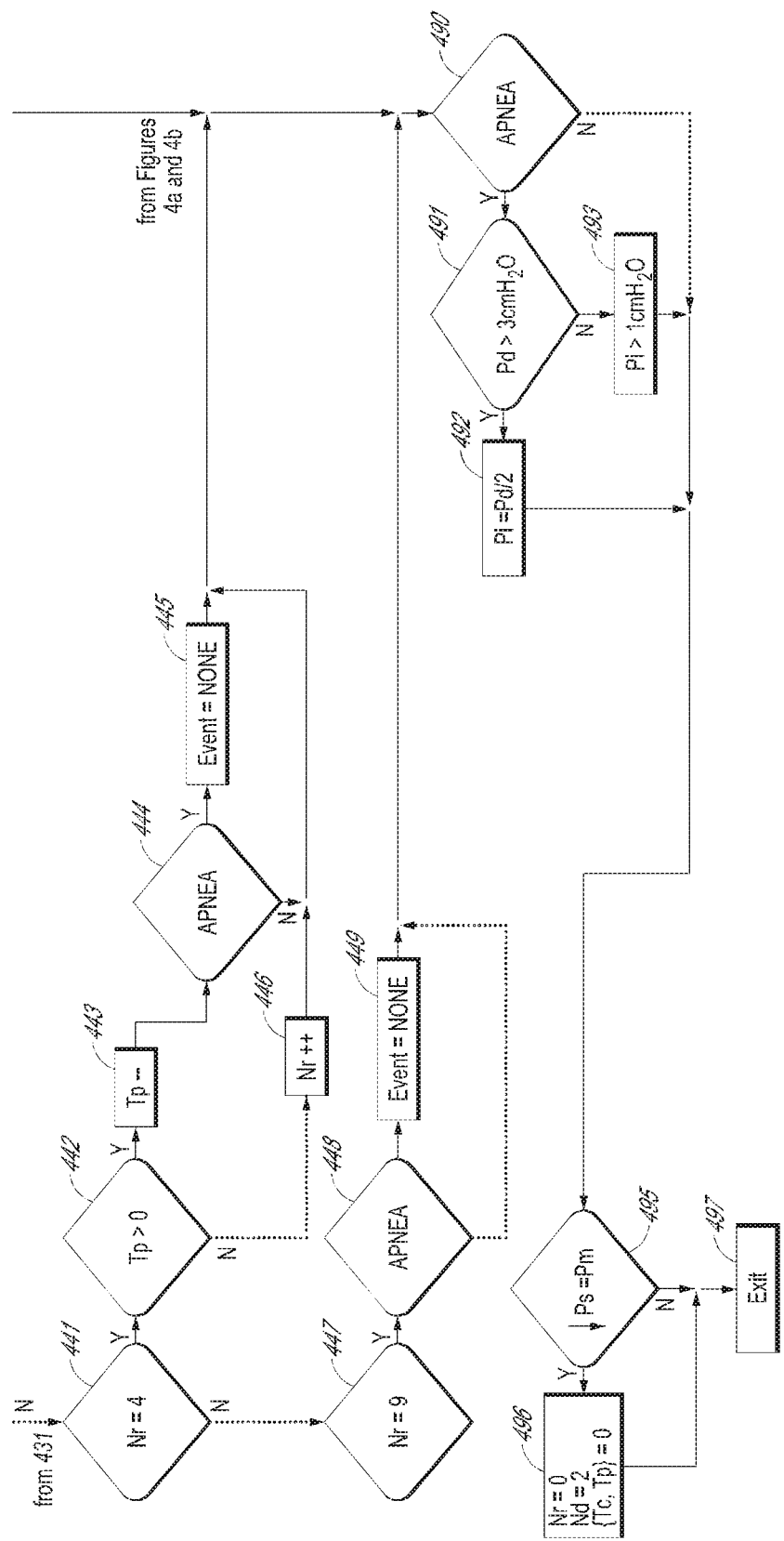

The preferred algorithm is illustrated in FIGS. 3a to 3c. In the preferred algorithm, the effect that the algorithm has on the event variable depends on an apnea response state. The apnea response algorithm maintains the apnea response state as the value of variable Nr. The algorithm progressively moves through apnea response states in response to particular patterns of apneas and non flow-limited hypopneas. In each of the apnea response states, the algorithm has a process for determining whether to replace an Event equals "apnea" value with an Event equals "none" value and whether to increase to the next response state. Independently, a portion of the algorithm has steps for deciding whether to step back one apnea response state in response to an Event equals "normal" value. The algorithm also has additional functionality to improve the response to apneas that arise at a time when pressure is being relieved due to the sensing of patient arousal or awakening and steps to completely reset the response state if the pressure returns to the minimum set pressure due to periods of normal breathing.

Looking at the illustrated algorithm in detail, the apnea response algorithm is entered at step 401. As noted previously, the algorithm is run repetitively and, by way of example, might be run every 20 ms.

The algorithm proceeds to step 402 and compares a pressure decrease variable Pd against a threshold value, for example 3 cmH$_2$O. The pressure decrease variable represents an amount of decrease that has occurred immediately recently in relieving pressure in response to sensing patient arousal or awakening. The subsequent loop, or loops, at steps 403 and 404 and a further loop involving steps 490 to 493 determines the effect that this situation has on the apnea response state and a subsequent pressure increase responding to any new apnea.

In particular, steps 403 and 404 would determine that if the apnea response state is greater than 3, then the apnea response state becomes 3, the timers (Tc and Tp) used in the apnea response algorithm are reset to 0 and a normal breathing counter Nd is set at 2, requiring two periods of normal breathing before reduction will occur in the apnea response state. This value for the normal breathing counter is essentially the reset value.

This apnea response state (Nr=3) is a state immediately before the algorithm will enter a pause state, allowing settling of patient airways. Accordingly, a pair of apnea or non flow-limited hypopnea events within a triggering time period will then cause the algorithm to enter the pause state but allow the controller to respond to the second event.

Returning the apnea response state to 3 in the case of a large pressure reduction following patient arousal brings the algorithm back into a state that can respond to further events.

So at step 402, the algorithm decides whether the recorded pressure decrease Pd is greater than 3cmH$_2$O. If so, the algorithm proceeds to step 404 and decides whether the apnea response state is greater than 3. If it is, then the algorithm proceeds to step 404, resets the apnea response state as 3, the normal breathing counter as 2 and the timers as 0. If a negative determination is made at step 402 or 403, the algorithm proceeds directly to step 405. Step 404 returns to step 405 after resetting the variables.

The set of steps 490 to 493 will now be described. This is out of order compared to how they occur within the rest of the algorithm, but is convenient because they also relate to how the algorithm responds in the case of patient arousal. Essentially, steps 490 to 493 set a customised pressure increase in response to an apnea (proceeded closely by an apnea or non-flow limited hypopnea) that occurs while the pressure is being decreased in response to an arousal. In particular, step 490 checks whether Event equals "apnea". If Event equals "apnea", the algorithm proceeds to step 491. Otherwise, the algorithm proceeds onward to step 495.

If Event equals "apnea" at step 490, the algorithm proceeds to step 491 and checks whether the pressure decrease is greater than 3cmH$_2$O. If the pressure decrease (so far) due to the arousal is not greater than 3cmH$_2$O, then the subsequent pressure increase Pi is set as 1 cmH$_2$O. Otherwise, the algorithm proceeds to step 492 and sets the pressure increase Pi as half the pressure decrease Pd. Steps 492 and 493 return to step 495 after setting the pressure increase variable Pi. The pressure increase variable Pi may be used in a subsequent pressure adjustment algorithm to override any alternative determination.

This part of the response is separated from the initial consideration of the effect of pressure decrease due to patient arousal at steps 402 to 404. These steps may not be triggered immediately, even if the interrupting event was an apnea, because the event variable may have been set from "apnea" to "none" by steps associated with the apnea response state. For example, if the arousal triggered step 404, then subsequent steps 434, 439 and 440 will set event to "none" before the process reaches step 490. That will be described.

Returning to consideration of step 405, at step 405, the algorithm determines whether Event equals "normal". Event equals "normal" indicates that the event detection algorithm has determined that breathing has been normal, with no sleep disorder events, for an immediately preceding predetermined period of time. In the preferred form, this period of time would be between 2 minutes and 5 minutes, most preferably about 2.5 minutes. The event detection algorithm will return an Event equals "normal" once only before resetting its normal breathing timer. An Event equals "normal" value will only be returned once each 2.5 minutes in the presence of sustained steady breathing.

If the algorithm determines that Event equals "normal" at step 405, the algorithm proceeds to step 406. At step 406, the algorithm decrements the normal breathing counter Nd by 1. The preset state for the normal breathing counter Nd is 2, and this step represents the only step in the apnea response algorithm which will decrement the normal breathing counter. Accordingly, the first iteration through step 406, the counter will be decremented from 2 to 1. On a subsequent occasion, the counter will be decremented from 1 to 0, unless the counter has been reset to 2 in the intervening period. The algorithm proceeds to step 407 and determines whether the counter is greater than 0. If the counter is greater than 0, then the algorithm takes no action and proceeds directly to step 490. Step 490 would inevitably determine false, and so the algorithm in fact proceeds to step 495.

The loop at steps 495 and 496 has the purpose of resetting the apnea response state when the set pressure drops to the minimum pressure. Changes in the set pressure that lead to the set pressure dropping to the minimum pressure are made in the pressure adjustment algorithm. These reductions could occur for at least two reasons. The first reason is periods of normal breathing, indicated by an event equals normal value and which usually leads to a decrement to the set pressure Ps. The other cause of reductions in pressure is in the case of pressure relief due to sensed arousals. In that case, pressure is reduced more rapidly, for example about 0.1cmH$_2$O per second.

At step 495, the apnea response algorithm determines whether the set pressure Ps has reached the minimum pressure Pm by decreases in value. If so, the algorithm proceeds to step 496, otherwise the apnea response algorithm exits at step 497. The algorithm will not proceed to step 496 on occasions where the set pressure equals the minimum pressure, but was already at the minimum pressure in a previous iteration. This ensures that the resetting function of step 496 only occurs once and does not override the effect of other parts of the apnea response algorithm.

For example, the set pressure will usually start at the minimum pressure. An initial apnea will lead to new settings for the apnea response state and the apnea trigger timer Tc, but not to a change in pressure. The set pressure is the minimum pressure so the comparison will not determine "true" because the set pressure has not reduced to that minimum pressure. Accordingly, the newly set variables Nr and Tc will not be inadvertently reset by step 496.

If, at step 407 the algorithm determines that the normal breathing counter has been decremented to 0, this indicates two consecutive periods of normal breathing. The algorithm then proceeds to step 408, resets the normal breathing counter to 2 and resets the apnea trigger timer Tc to 0, and most importantly, decrements the apnea response state Nr by 1. The algorithm then proceeds through to step 495.

The normal breathing counter Nd reaching 0 represents two consecutive periods of normal breathing. The effect of steps 409 and 410 is to reset the counter to 2 on any sleep disorder breathing event, meaning any value of the event variable other than normal and none. In particular, at step 409, the algorithm checks whether Event equals "none". If so, it proceeds directly to step 411. Otherwise, the algorithm proceeds to step 410 and resets the normal breathing counter Nd as 2.

The next core branch of the algorithm is to determine which steps to execute based on the present apnea response state Nr. This is represented by steps 411, 414, 423, 431, 441, 447, which determine whether the algorithm proceeds by associated paths 412 to 413, 415 to 421, 424 to 430, 432 to 440, 442 to 446 and 448 to 449 respectively. Each of these paths eventually returns to step 490, but in between may adjust the apnea response state Nr, the values of timers Tc and Tp and the value of the event variable.

Step 411 determines whether the apnea response state Nr equals 0 or 5. If so, the algorithm is in a sort of an initial state in which it will wait for a first apnea to occur and proceeds to step 412. If not, the algorithm proceeds to step 414.

If the algorithm determines at step 412 that Event does not equal "apnea", then it proceeds directly to step 490 and of course to step 495. Otherwise, the algorithm proceeds to step 413. At step 413, the algorithm increments the apnea response state, sets an apnea trigger timer Tc to a predetermined value, for example 2.5 minutes, and resets the event variable to "none". Resetting Event to "none" means that in the subsequent pressure adjustment algorithm, there will be no adjustment of the set pressure in response to the apnea that has been determined by the event detection algorithm. Resetting event variable to "none" also means that step 490 will determine false and the algorithm will proceed direct to step 495 without proceeding through steps 491 to 493 and looking at the magnitude of any pressure decreases due to arousal.

If the algorithm determined false at step 411, it proceeds instead to step 414 and determines whether the apnea response state is 1 or 6. If the apnea response state is 1 or 6, the algorithm proceeds to step 415 and decrements the apnea trigger timer Tc by an amount equivalent to the loop repeat time for the apnea response algorithm (for example, 20 ms). The algorithm then proceeds to step 416.

At step 416, the algorithm determines whether the apnea trigger time is greater than 0. The effect of steps 413, 415 and 416 is to only allow incrementing the apnea response state at step 418 if the apnea or non flow-limited hypopnea (checked at step 417) occurred within 2.5 minutes of the apnea determined at check 412. Otherwise, the algorithm proceeds from step 416 to 419 and decrements the apnea response state Nr by 1. This reverts the apnea response state to 0 because no apnea occurred within the 2.5 minute trigger window.

Proceeding from step 419 to step 420, the algorithm determines whether Event equals "apnea" in the particular execution (with a very low probability). If so, the algorithm replaces Event equals "apnea" with Event equals "none" at step 421.

In the case of a negative determination at step 420, or after the executing step 421, the algorithm proceeds to step 490 and therefore to step 495.

If the timer Tc had not run out at step 416, the algorithm proceeds instead to step 417 and checks whether the event variable equals "apnea" or "non flow-limited hypopnea". If not, the algorithm proceeds directly to step 490 and therefore step 495 without making any further adjustments.

If Event does equal "apnea" or "non flow-limiting hypopnea", the algorithm proceeds from step 417 to step 418 and increments the apnea response state and resets the apnea trigger timer to 2.5 minutes. The apnea or non flow-limited hypopnea has occurred within 2.5 minutes of the apnea found at check 412. Accordingly, the apnea response state increases and a new apnea trigger timer is set. Again, the preferred predetermined value for the apnea trigger timer is 2.5 minutes. Other values between, for example, 1 minute or 5 minutes may be appropriate.

The value of the event variable is not reset and remains as "apnea" or "non flow-limiting hypopnea". Accordingly, the set pressure will be incremented in the pressure adjustment algorithm.

After step 418, the algorithm proceeds to step 490. In this instance, Event may equal "apnea", so the algorithm may check whether the apnea has occurred during a pressure reduction sequence resulting from patient arousal.

At step 414, if the apnea response state is not 1 or 6, the algorithm proceeds to step 423 and determines whether the apnea response state is 2 or 7. If so, the algorithm proceeds to the process of step 424 to 430. These steps are largely similar to steps 415 to 421 for apnea response states 1 and 6 except that these steps do not provide for decrementing the apnea response state Nr by the lapse of time alone (which is the effect of steps 416 and 419). Instead, the algorithm will remain in this response state (2 or 7) indefinitely unless the response state is either increased (step 427 which will be described shortly) or decreased elsewhere, such as at step 408 or reset at step 496. As already discussed, decrementing at step 408 is in response to consecutive periods of normal breathing, while eventual resetting at step 496 is in response to the set pressure reducing to the minimum pressure.

An increase in the apnea response data at step 427 occurs if an apnea or a non flow-limited hypopnea occurs within the predetermined apnea trigger time of the apnea or non flow-limiting hypopnea determined at step 417 or the last apnea or last non flow-limiting hypopnea determined at step 425 while in the present apnea response state. From step 423, the algorithm proceeds to step 424 and decrements apnea trigger timer Tc. The algorithm then proceeds to step 425 and checks whether Event equals "apnea" or Event equals "non flow-limiting hypopnea". If not, the algorithm proceeds to step 495. Otherwise, if Event does equal "apnea" or "non flow-limiting hypopnea", the algorithm proceeds to step 426 and checks whether the apnea trigger timer is still greater than 0.

If the apnea trigger timer is greater than 0, the algorithm proceeds to step 427 and increments the apnea response state Nr and then proceeds to step 428 and resets the apnea trigger timer to the preset apnea trigger time, for example, 2.5 minutes. The algorithm then proceeds from step 428 to step 495.

If the algorithm determined at step 426 that the apnea trigger time had expired (Tc is equal to or less than 0), the algorithm proceeds to step 429 and 430.

If the algorithm determines at step 429 that Event equals "apnea", the algorithm resets event to "none" at step 430.

Then, or otherwise, the algorithm proceeds to step 428 and resets the trigger timer Tc to the predetermined trigger time.

The effect of steps 429 to 430 is to ensure that the pressure adjusting algorithm does not increment the set pressure in response to the apnea that was found not to have occurred within the apnea trigger time. The effect of bypassing step 427 where the apnea trigger timer has expired at step 426 is that the apnea response state Nr is unchanged. Resetting the trigger timer at step 428 is either effective when waiting for an apnea or non flow-limiting hypopnea in the next apnea response state, or in the continuing time within the present apnea response state.

If at step 423 the apnea response algorithm determines that the apnea response state Nr is not 2 or 7, the algorithm proceeds to step 431 to determine whether the apnea response state is 3 or 8. If so, the algorithm proceeds to step 432. Otherwise, it proceeds to step 441. The method of steps 432 to 438 is broadly similar to the method of steps 424 to 430 except for the inclusion of additional steps 435 and 436 which prepare an additional pause timer for the next response state.

So proceeding from step 431, the algorithm proceeds to step 432 and decrements apnea trigger timer Tc. The algorithm then proceeds to step 433 and checks whether Event equals "apnea" or Event equals "non flow-limiting hypopnea". If not, the algorithm proceeds to step 495. Otherwise, if Event does equal "apnea" or "non flow-limiting hypopnea", the algorithm proceeds to step 434 and checks whether the apnea trigger timer is still greater than 0.

If the apnea trigger timer is greater than 0, the algorithm proceeds to step 435 and checks whether the apnea response state Nr equals 3. If Nr equals 3, the algorithm proceeds to set a pause timer Tp. The pause timer Tp will be active in the next apnea response state. The pause timer Tp sets the duration of the pause, and in the example Tp is set to 5 minutes. The algorithm then proceeds to step 437.

If Nr did not equal 3 at step 435, the algorithm would proceed directly to step 437.

At step 437, the algorithm increments the apnea response state Nr and then proceeds to step 438 and resets the apnea trigger timer to the preset apnea trigger time, for example, 2.5 minutes. The algorithm then proceeds from step 438 to step 495.

If the algorithm determined at step 434 that the apnea trigger time had expired (Tc is equal to or less than 0), the algorithm proceeds to step 439 and 440.

If the algorithm determines at step 439 that Event equals "apnea", the algorithm resets event to none at step 440.

Then or otherwise, the algorithm proceeds to step 438 and resets the trigger timer Tc to the predetermined trigger time.

The effect of steps 439 to 440 is to ensure that the pressure adjusting algorithm does not increment the set pressure in response to the apnea that was found not to have occurred within the apnea trigger time. The effect of bypassing steps 435 to 437 where the apnea trigger timer has expired at step 434 is that the apnea response state Nr is unchanged. Resetting the trigger timer at step 438 is either effective when waiting for an apnea or non flow-limiting hypopnea in the next apnea response state, or in the continuing time within the present apnea response state.

In response states 3 and 8, the algorithm includes an additional step between checking whether the apnea trigger timer has expired and incrementing the response state. This step could be performed after incrementing the response state with minor adjustment. This step checks the present response state at step 435 to determine if the next response state (the state that will prevail in the next execution of the algorithm) will be 4.

If the next response state will be 4, for example because the current response state is 3, with the step 435 in the illustrated location, then at step 436 the algorithm sets a pause time timer Tp with an initial value. Preferably the initial value is between 3 minutes and 10 minutes and may, for example, be 5 minutes.

If the next apnea response state will not be 4, then the step of setting the pause timer is omitted and the algorithm proceeds directly from step 435 to 437. If the step of initiating the pause timer is provided after the step 437 of increasing the apnea response state, then the equivalent to step 435 would check whether the apnea response state equals 4 rather than 3.

Initiating the pause timer from the previous response state could be omitted in favour of a single execution initiation elsewhere in the algorithm, for example, within the part of the algorithm that is executed if the response state is 4. However in that case, correctly setting and resetting that variable may be more difficult than where it is initiated upon exiting the immediately preceding response state. As with equivalent steps 425 and 417, if at step 433 the event is not an apnea or non flow-limited hypopnea, the algorithm proceeds directly to step 495.

In the preferred embodiment of the invention, two sequences of apnea are allowed for, with a pause state between, and followed by a longer term non-responsive state. Apnea response state 3 immediately precedes the pause state 4 while apnea response state 8 immediately precedes the non-responsive apnea response state 9. For the non-responsive apnea response state 9, no automatic change of state is provided based on a timer alone. Accordingly, there is no need to set a pause timer.

In iterations where the apnea response state is 4, the algorithm passes through steps 411, 414, 423 and 431 and determines at step 441 that the apnea response state equals 4 and proceeds to step 442. The collection of steps 442 to 446 implements a pause state where the algorithm will not respond to apneas for a period of time to allow the patient airway to stabilise. This time is set by the pause timer Tp, which is set at step 436.

At step 442, the algorithm determines whether the timer has expired by checking whether Tp is greater than 0. If Tp is greater than 0, then the timer has not expired and the algorithm proceeds to step 443 and decrements the timer. The algorithm then proceeds to step 444 and determines whether Event equals "apnea". If Event equals "apnea", the algorithm replaces this with Event equals "none" at step 445. If Event does not equal "apnea" at step 444, the algorithm proceeds directly to step 495. If at step 442, the timer has expired (Tp is less than or equal to 0), then the algorithm proceeds to step 446 and increments the apnea response state so that the next apnea response state will be 5 and in the next iteration the algorithm will look for an apnea to set an apnea trigger timer at step 413.

Where the apnea response state has progressed from state 8 to state 9 (at steps 437), in the next iteration the algorithm will proceed through steps 411, 414, 423, 431 and 441 and determine at step 447 that the apnea response state is 9. Alternatively step 447 can be omitted, assuming that only apnea response states between 0 and 9 are possible. In that case, the algorithm proceeds to step 448 and checks whether Event equals "apnea". If Event equals "apnea", the algorithm resets Event to "none" at step 449. This ensures that the pressure adjustment algorithm does not respond to apneas determined while the apnea response state is 9. No other adjustments are made. The apnea response state can only reduce from 9 by operation of steps 495 and 496 (pressure returning to minimum pressure), steps 402 to 404 (pressure drop due to patient arousal), or steps 405 to 408 (extended periods of normal breathing).

Operating in the manner described, the algorithm can be seen to amend the Event variable from "apnea" to "none" at steps 413, 421, 430 and 440 unless it was preceded by less than 2.5 minutes by another apnea or non flow-limiting hypopnea. Accordingly, response to a pattern of apneas does not commence until an apnea is succeeded by an apnea or non flow-limiting hypopnea within a period of less than 2.5 minutes. This initial apnea is determined at step 412 and the timer set at step 413. The subsequent apnea, within the timer period, is determined at step 417. Otherwise, all other apneas are not responded to due to re-writing Event to "none" at steps 413 and 421. While the algorithm is in the pause state (Nr equals 4), response to all apneas is suppressed by replacing Event equals "apnea" with Event equals "none" at step 445. While in a definite non-responsive state (Nr equals 9), response to all apneas is suppressed by replacing Event equals "apnea" with Event equals "none" at step 449.

Accordingly, the algorithm illustrated in detail in FIG. 4 implements the principles described earlier, within an overall control where the apnea response algorithm is preceded by an event detection algorithm and succeeded by a pressure adjusting algorithm. Examples of particular event detection algorithms and pressure adjusting algorithms are known in the art.

The event modification algorithm is described here as an example. Modification may be required according to the particular characteristics of the event detection algorithm and pressure adjusting algorithm. For example, if the overall control scheme implements pressure adjustments immediately after determining an event, one appropriate implementation might involve determining the apnea response by applying the outlined principles against a record of preceding events.

Other overall control architectures for responding to apneas incorporating the present inventions are possible.

The controls according to the present invention may be implemented in typical gases supply systems, in particular in the control programs executed in the flow generator. An example system and flow generator will be described with reference to FIG. 1.

Figure 1:
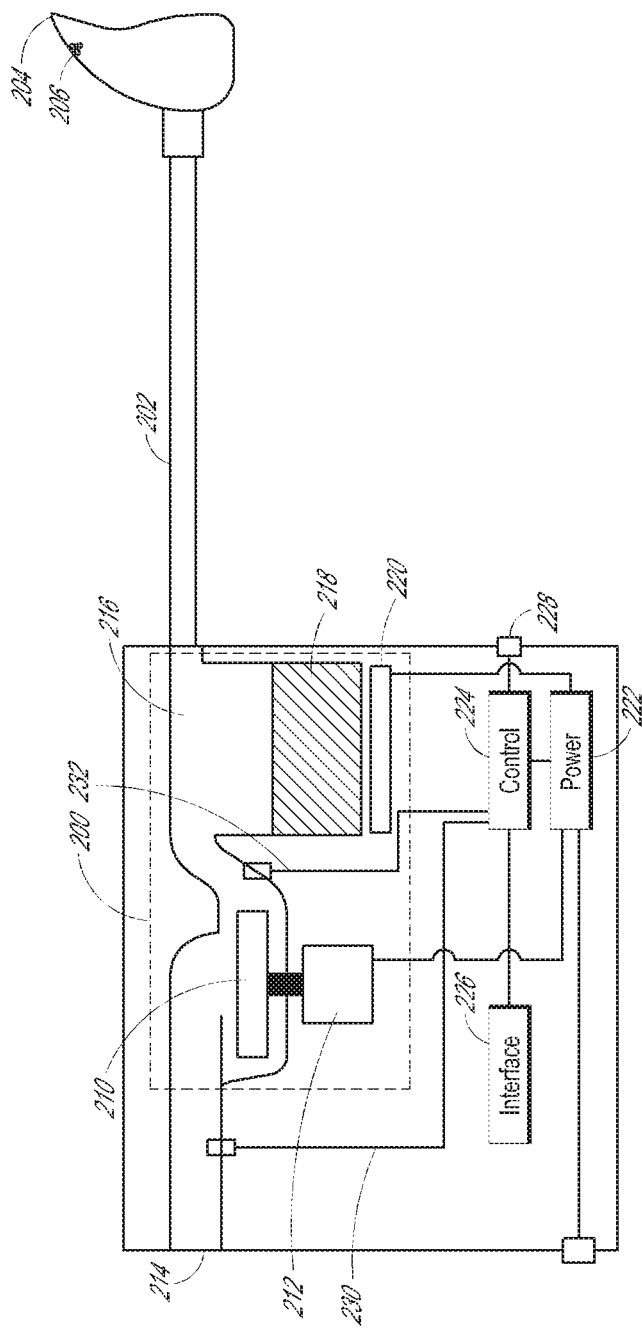
FIG. 1 is an illustration of a patient receiving PAP therapy from a system including a flow generator, a patient interface and a conduit connecting between the patient interface and the flow generator.

FIG. 1 is a block diagram illustrating a preferred embodiment of a breathing gases supply system of a type that may incorporate the present invention. The full system includes an apparatus 200 for delivering a supply of breathing gases, a supply conduit 202 and a patient interface 204.

The supply conduit 202 extends from an outlet of the gases supply apparatus to the patient interface.

The patient interface includes a bias flow vent 206 for allowing a controlled leak from the patient interface 204. The controlled leak allows the inside of the patient interface 204 to be continuously flushed by fresh gases supplied by the supply apparatus 200. The patient interface 204 may comprise any of the many types of typical patient interface for PAP delivery, for example, nasal mask, full face mask, oral mask, oral interface, nasal pillows, nasal seal or nasal cannula.

The bias flow vent 206 may be located directly on the patient interface, or adjacent the patient interface on a connector between the patient interface 204 and the supply tube 202 or through the wall of the supply tube 202, close to the patient interface 204. A wide variety of patient interfaces and conduits are known in the art.

The supply apparatus 200 includes a flow generator. The preferred flow generator comprises a fan 210 driven by an electric motor 212. Air is drawn through an inlet 214 in the housing of the apparatus by the fan 210. Pressurised air leaves the fan 210 for supply to the patient. Alternatively, controllable flow generators may draw on a source of high pressure gas, and regulate a flow of gas from the high pressure source.

The apparatus 200 may include a humidifier 216, for example in the form of a pass-over humidifier where air passing through the humidifier chamber picks up a quantity of water vapour from a reservoir of water 218. The water reservoir 218 may be heated by a heater 220. The humidifier may be integrated with the housing of the flow generator or a separate, optional, component.

The heater 220 and motor 212 are supplied with power from a power supply 222. The amount of power to the motor and the amount of power to the heater are controlled by outputs of controller 224.

The controller 224 is also supplied with power from the power supply 222.

The controller 224 receives input from a user interface 226.

The controller 224 may also include an interface 228 for connecting with an external data source. The external data source may, for example, be a communication interface such as a modem, or may be an interface to an external memory such as a smart card, disk drive, flash memory or the like. For generic use, the interface 228 may be a data communication port according to any of the many available standards, for example, a universal serial bus (USB) port. A USB (or similar) interface can be used for connecting a wide range of peripheral devices.

The controller 224 typically includes an embedded microcomputer with stored control programmes.

The controller preferably includes interfaces for receiving input from a user interface 226 and for receiving input from one or more sensors which preferably include a flow sensor 230 and may also include a pressure sensor 232 downstream of the fan. The flow sensor 230 may be upstream or downstream of the fan.

According to the preferred embodiment of the invention, the apparatus is configured to perform control methods in the form of a control programs executable by the microcomputer of the controller 224.

Alternatively, the controller 224 may comprise a fixed electronic circuit implementing the control programs, or a programmed logic circuit (such as an FPGA) implementing the control programme. Electronic circuits and logic circuits implementing the control programme may be readily devised by persons skilled in the art.

Figure 4A:
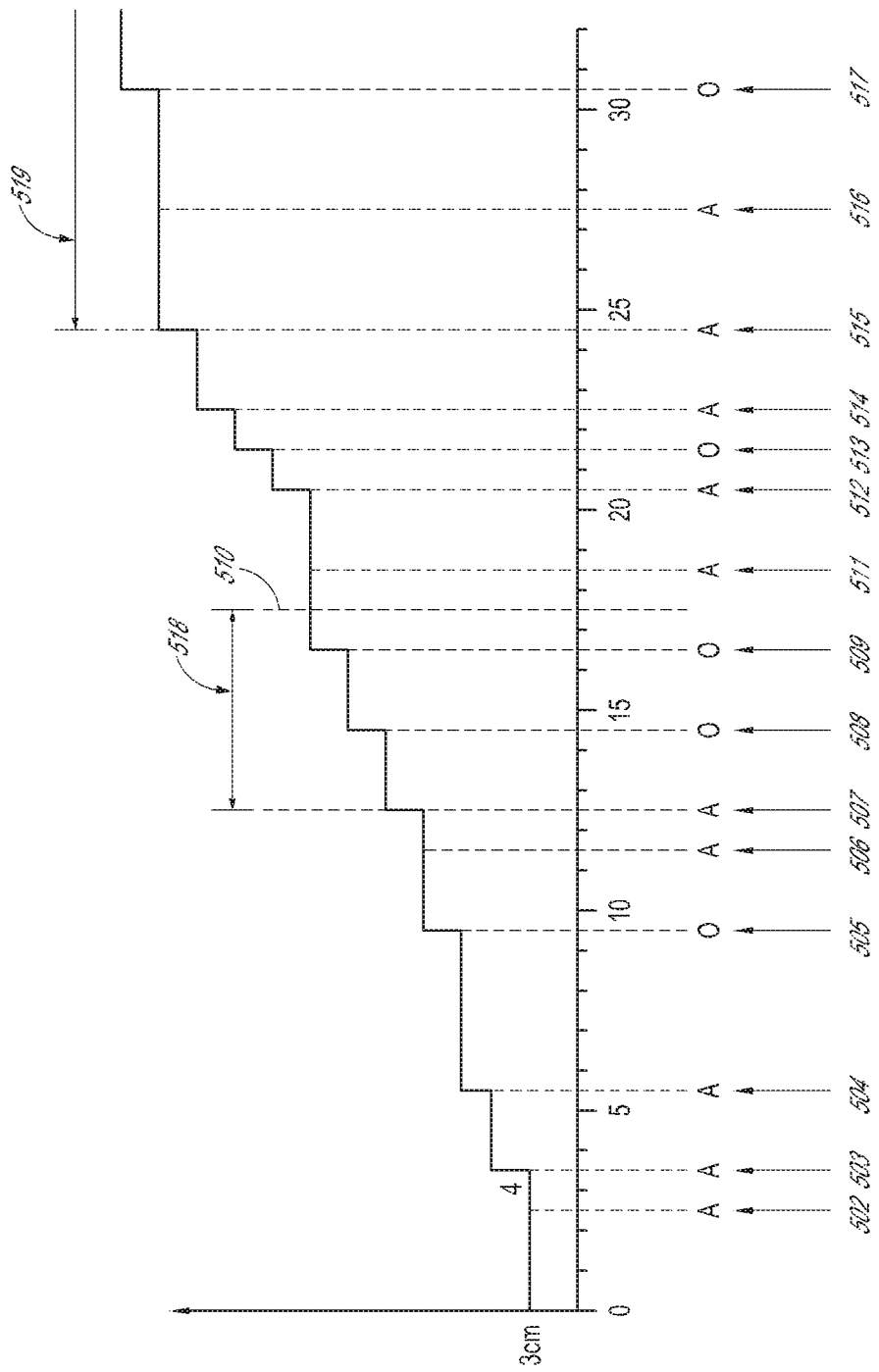
FIGS. 4a to 4c are plots of pressure against time illustrating the effect of sequences of events on the delivered therapy pressure.
Figure 4B:
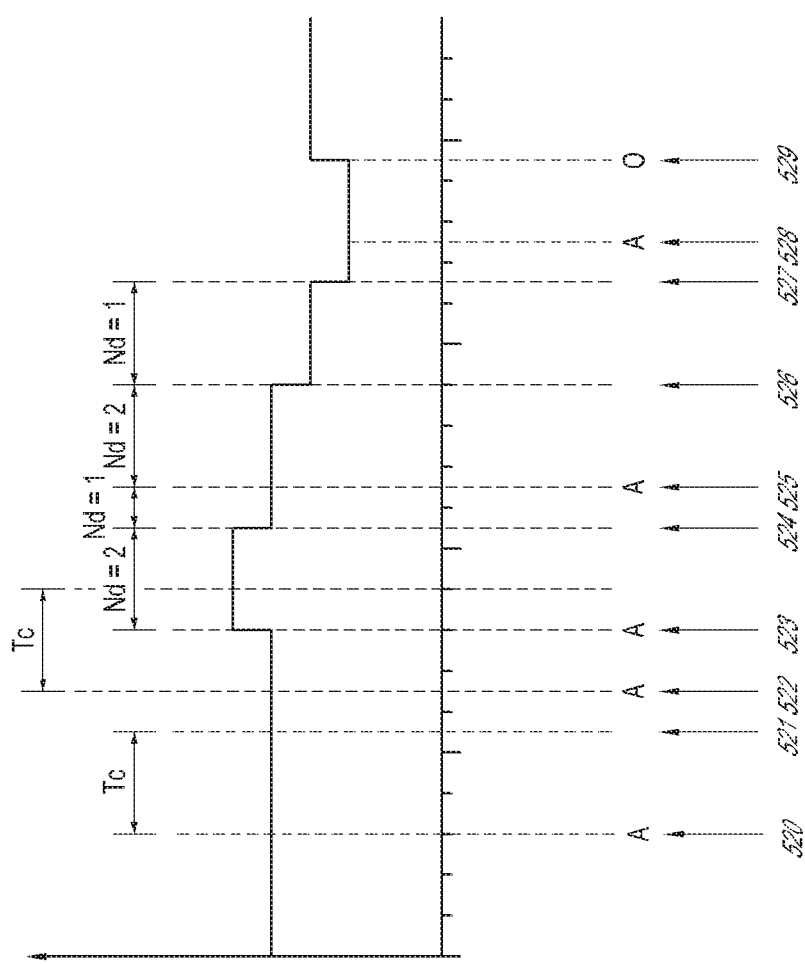
Figure 4C:
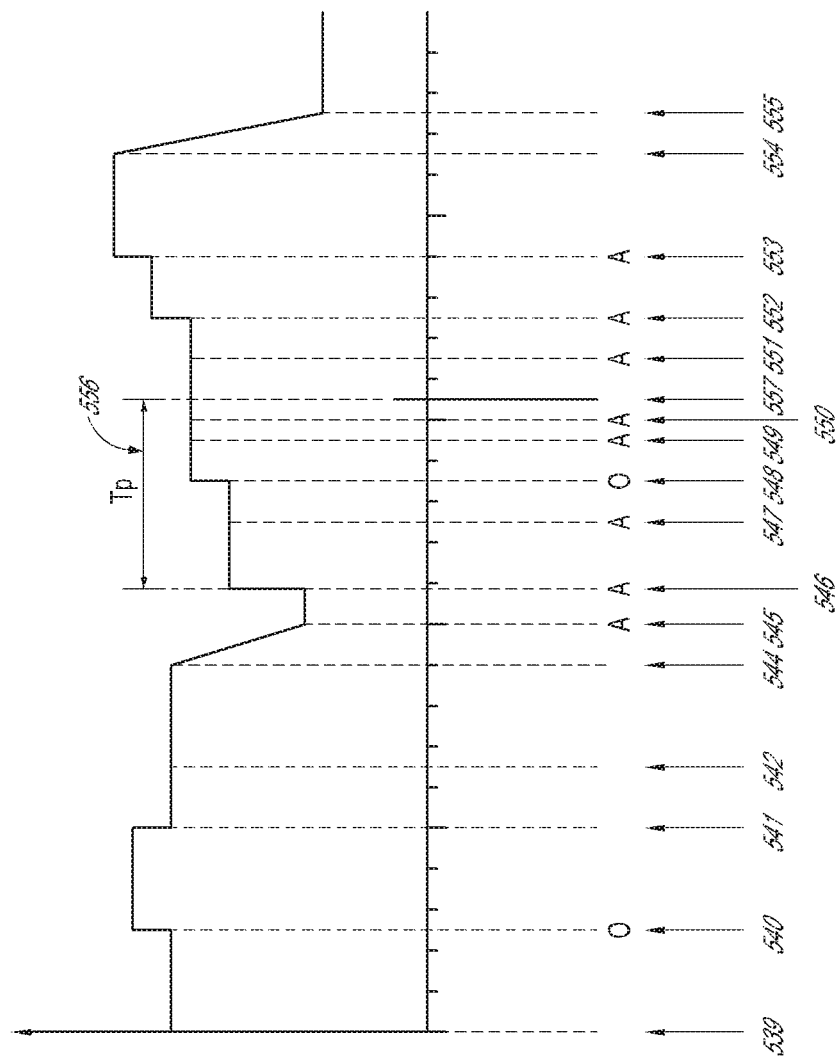

FIGS. 4a to 4c illustrate how the described system responds to hypothetical sequences of events. Each sequence, and the response will be described briefly. For simplicity, the sequence is limited to three types of events, apneas, obstructed breathing and periods of normal breathing. Apnea events are designated "A", obstructed breathing events (flow limitations) are designated "0".

FIG. 4a illustrates progression from an initial low pressure, through a series of pressure increases in response to events. The effect of the non-responsive state is exemplified. In FIG. 4a, the algorithm responds as follows:

| Event/Time | State/Action |
|---|---|
| 502 | No proceeding apnea. Sets trigger time Tc to 2.5 minutes but event resets to None. $N_R$ increases to 1. |
| 503 | $N_R$ increases to 2, Event stays "apnea", resets trigger timer to 2.5 minutes. |
| 504 | $N_R$ increases to 3, Event stays "apnea", resets trigger timer to 2.5 minutes. |
| 505 | $N_R$ stays 3, Event stays "obstructed breathing", does not reset trigger. |
| 506 | Trigger timer has expired, $N_R$ stays 3, Event is overwritten to "None" so pressure does not increase, resets trigger timer. |
| 507 | Trigger timer has not expired, $N_R$ increases to 4, Event stays "apnea" so pressure increases, control enters suppressed state |

-continued

| Event/Time | State/Action |
|---|---|
| | (518). |
| 508 | $N_R$ stays 4, Event stays "obstruction" so pressure increases. |
| 509 | $N_R$ stays 4, Event stays "obstruction" so pressure increases. |
| 510 | $N_R$ = 5, as the suppressed state timer Tp has expired. |
| 511 | $N_R$ = 6, Tc = 2.5 minutes, Event = None, pressure stays. |
| 512 | $N_R$ = 7, Tc = 2.5 minutes, Event stays apnea, pressure increases. |
| 513 | $N_R$ = 7, Tc unchanged, Event stays = Obstructive, pressure increases. |
| 514 | $N_R$ = 8, Tc resets to 2.5 minutes, pressure increases, Event stays apnea. |
| 515 | $N_R$ = 9, Tc = 2.5 minutes, Event stays apnea, pressure increases, indefinite suppression of response to apnea begins. |
| 516 | Ignored apnea as $N_R$ = 9 |
| 517 | $N_R$ = 9, Event stays "obstruction", pressure increases. |

The first non-responsive state is illustrated as period 518 in FIG. 4*a*. In this pause state, response to apnea is suppressed, but the algorithm still responds to obstructed breathing at 508 and 509.

The second non-responsive state is indicated as period 519, which commences with the apnea event at 515. In this non-responsive state, response to apneas is suppressed, for example, ignoring the apnea at 516, but the algorithm still responds to obstructed breathing at 517.

FIG. 4*b* illustrates progression during a sequence of more widely spread events. The figure plots set pressure against time. The sequence of events and the algorithm response is summarised in the following table:

| Event/Time | State/Action |
|---|---|
| 520 | Apnea starts timer Tc. Response state goes to $N_R$ = 1. |
| 521 | Timer Tc expires, response state goes to $N_R$ = 0. |
| 522 | Apnea starts timer Tc. Response state goes to $N_R$ = 1. |
| 523 | Apnea occurs before timer Tc expires. Response state goes to $N_R$ = 2, Event = apnea is not overwritten, pressure increases. |
| 524 | Event = Normal (following 2.5 minutes f normal breathing), $N_d$ decrements from 2 to 1. |
| 525 | Apnea resets $N_d$ to 2 and resets timer Tc to 2.5 minutes. There is no increase in response state. Event is overwritten to None, so no pressure increase results. |
| 526 | Normal breathing for 2.5 minutes leads to decrement $N_d$ to 1. |
| 527 | Normal breathing for 2.5 minutes leads to decrement $N_d$ to 0, which leads to $N_R$ decrement to 1. The pressure also decreases (independent of $N_R$) In nearly all cases, the response state will immediately change to 0 on next iteration of the algorithm. |
| 528 | Apnea. $N_R$ increases to 1, Tc = 2.5 minutes. Event is overwritten to None, so no pressure increase results. |
| 529 | $N_R$ stays 1, pressure increases. Tc unchanged. |

The sequence of 4*b* shows how the response state can fluctuate up and down according to frequency of triggering events and can fluctuate independently of the set pressure.

FIG. 4*c* illustrates progression during a period of normal breathing, and during and after two periods of patient arousal. In FIG. 4*c* the algorithm responds as follows:

| Event/Time | State/Action |
|---|---|
| 539 | The sequence commences with the set pressure at 14 cmH$_2$O and $N_R$ = 9. Accordingly, there is an indefinite suppression of response to apneas. |
| 540 | Responds to obstruction with increase in pressure to 15 cmH$_2$O. |
| 541 | 2.5 minutes after obstruction, normal event is returned, pressure is reduced and Nd reduces to 1. |
| 542 | $N_R$ = 9, Event = Apnea is overwritten to None. |
| 544 | Patient arousal responded to by rapid (0.1 cmH$_2$O per second) decrease in set pressure. |
| 545 | Apnea detected. Pressure reduction cycle ends prematurely at 7 cmH$_2$O. Pressure drop $P_D$ was 8 cmH$_2$O. $P_D$ > 3 CMH$_2$O => NR resets to 3, and Tc set to 2.5 minutes. |
| 546 | Another apnea detected. $N_R$ increases to 4 and apnea is not reset. Pi is set to 4 cmH$_2$O. Pressure increases by 4 cmH$_2$O. |
| 547 | Apnea is ignored as $N_R$ = 4 and pause state 556 is in effect. |
| 548 | Obstruction leads to increase in set pressure. |
| 549 | Apnea is ignored as $N_R$ = 4. |
| 550 | Apnea is ignored as $N_R$ = 4. |
| 557 | Pause state ends, $N_R$ increases to 5. |
| 551 | Apnea is ignored. $N_R$ increases to 6. |
| 552 | Apnea is responded to. Apnea occurred less than 2.5 minutes after apnea at 551. Response state increases to 7. Pressure is increased. |
| 553 | Apnea is responded to. Apnea occurred less than 2.5 minutes after apnea at 552. Response state increases to 8. Pressure is increased. |
| 554 | Patient arousal detected. Leads to a rapid reduction in set pressure. |
| 555 | Set pressure reaches Pm (3 cmH$_2$O). $N_R$ resets to 0. |

What is claimed is:

1. A method for controlling an automatically adjusting PAP apparatus, comprising:
    operating a controller in a first responsive state in which the controller is configured to respond to a first series of non-isolated apneas and/or non-isolated non-flow limited hypopneas by increasing an output pressure of a gases flow source;
    increasing a counter in response to non-isolated apneas and/or non-isolated non-flow limited hypopneas; and
    entering a pause state when the counter exceeds a threshold, the pause state having a predefined duration, wherein during the pause state, the controller increases the output pressure of the gases flow source in response to flow-limited breaths and non-flow limited hypopneas but does not increase the output pressure in response to apneas.

2. The method of claim 1, further comprising decreasing the counter in response to nominal periods of normal breathing.

3. The method of claim 1, wherein increasing the counter in response to non-isolated apneas and/or non-isolated non-flow limited hypopneas comprises increasing the counter in response to an apnea or non-flow limited hypopnea preceded by another apnea or non-flow limited hypopnea within a predetermined period of time.

4. The method of claim 3, wherein the predetermined period of time is 2.5 minutes.

5. The method of claim 1, further comprising increasing the counter in response to a first apnea detected after entering the pause state.

6. The method of claim 5, further comprising increasing the counter in response to an apnea or non-flow limited hypopnea detected within a predetermined period of time after the first apnea detected after entering the pause state.

7. The method of claim 6, wherein the predetermined period of time is 2.5 minutes.

8. The method of claim 1, further comprising increasing the counter in response to a first apnea detected after the counter has been reset.

9. The method of claim 8, further comprising increasing the counter in response to an apnea or non-flow limited hypopnea detected within a predetermined period of time after the first apnea detected after the counter has been reset.

10. The method of claim 9, wherein the predetermined period of time is 2.5 minutes.

11. The method of claim 1, further comprising increasing the counter by an increment of one upon expiration of the pause state.

12. The method of claim 1, further comprising after the pause state, operating the controller in a second responsive state in which the controller is configured to respond to a second series of non-isolated apneas by increasing an output pressure of the gases flow source.

13. The method of claim 1, wherein the controller is configured not to increase the output pressure of the gases flow source in response to non-flow limited hypopneas when the gases flow source has reached a pressure limit, the pressure limit independent of response to apneas.

\* \* \* \* \*